United States Patent [19]

Pergande et al.

[11] Patent Number: 6,034,112
[45] Date of Patent: Mar. 7, 2000

[54] USE OF FLUPIRTINE THE PROPHYLAXIS AND THERAPY OF DISEASES ASSOCIATED WITH AN IMPAIRMENT OF THE HEMATOPOETIC CELL SYSTEM

[75] Inventors: Gabriela Pergande, Offenbach; Werner E. G. Müller, Wiesbaden, both of Germany

[73] Assignee: ASTA Medica Aktiengesellschaft, Dresden, Germany

[21] Appl. No.: 09/061,099

[22] Filed: Apr. 16, 1998

Related U.S. Application Data

[63] Continuation of application No. 08/744,953, Nov. 7, 1996.

[30] Foreign Application Priority Data

Nov. 7, 1995 [DE] Germany .......................... 195 41 405

[51] Int. Cl.[7] .................................................. A01N 43/40
[52] U.S. Cl. .............................................................. 514/353
[58] Field of Search .............................................. 514/353

[56] References Cited

PUBLICATIONS

Perovic et al., 1995, 122 CA:46354.

*Primary Examiner*—Russell Travers
*Attorney, Agent, or Firm*—Pillsbury Madison & Sutro, LLP

[57] ABSTRACT

The invention relates to the use of flupirtine or its salts as drugs in the prophylaxis and therapy of diseases associated with an impairment of the haematopoetic cell system, for example lymphocytes.

Especially important in this respect is the treatment of HIV infected patients/AIDS patients.

3 Claims, 2 Drawing Sheets

USE OF FLUPIRTINE THE PROPHYLAXIS AND THERAPY OF DISEASES ASSOCIATED WITH AN IMPAIRMENT OF THE HEMATOPOETIC CELL SYSTEM

This application is a continuation of Ser. No. 08/744,953 filed Nov. 3, 1996.

This application is based on application no. 19541405.5 filed in Germany on Nov. 7, 1995, the entire content of which is incorporated hereinto by reference.

BACKGROUND OF THE INVENTION

1. Field of the Invention

The present invention relates to the use of flupirtine or its salts as medicaments in the prophylaxis and therapy of diseases associated with an impairment of the haematopoetic cell system, for example lymphocytes.

2. Background Information

Flupirtine is a known, established, non-opiate analgesic with central action.

Flupirtine expresses its analgesic actions by different mechanisms from the opiate/opioid analgesics (Nickel, B., Postgrad, Med. J. 63 (Suppl.3), 19 (1987); Szelenyi, I., Nickel, B., Borbe, H. O., Brune K., Br. J. Pharmacol. 143, 89 (1989)). Electrophysiological studies have shown that flupirtine is able to influence nociceptive events at the supraspinal level as well as at the spinal level (Carisson, K. H., Jurna, I., Eur. J. Pharmakol. 143, 89 (1987); Bleyer, H., Carlsson, K. H., Erkel, H. J., Jurna, I., Eur. J. Pharmacol. 151, 259 (1988); Nickel, B., Aledter, A., Postgrad Med. J. 63 (Suppl.3) 41 (1987)).

Flupirtine is also used in the therapy of periods of acute pain caused by diseases of the locomotion system.

Furthermore, flupirtine is successfully used in patients with degenerative or rheumatic diseases.

In addition to having good analgesic properties, flupirtine also has muscle-relaxant properties, so that flupirtine can also be used in the treatment of muscular tension, or of diseases caused by muscular tension (DE 40 22 442).

In studies of the muscle relaxant action of flupirtine in rats it was further found that the action of flupirtine can be inhibited by the excitatory amino acid N-methyl-D-aspartate (NMDA). Due to this NMDA antagonistic action, flupirtine is also suitable for the treatment of NMDA mediated diseases of the CNS, such as cerebral ischaemia, neurodegenerative disorders and epileptic fits (DE 43 27 516).

In chemical terms, flupirtine is 2-amino-3-ethoxycarbonylamino-6-(p-fluorobenzylamino)pyridine. The synthesis of flupirtine and its pharmaceutically usable salts is described in the patents DE 17 95 858, DE 31 33 519 and DE 34 16 609.

SUMMARY OF THE INVENTION

Surprisingly, it has now been found that flupirtine is able to inhibit apoptotic cell death in the haematopoetic system, for example in lymphocytes.

This opens up the prospect of using flupirtine in the treatment of diseases associated with the impairment of the haematopoetic cell system.

Especially important in this respect is the treatment of HIV infected patients/AIDS patients.

DETAILED DESCRIPTION OF THE INVENTION

The novel action according to the invention will now be illustrated in pharmacological studies.

Pharmacological Studies

Materials

Flupirtine maleate [2-amino-3-ethoxycarbonyl-amino-6-(p-fluorobenzylamino)pyridine maleate], for the preparation of HIV-1-gp120, the HIV-1 virus strain $HTLV_{IIIB}$ was used (Popovic et al., 1984). The resulting isolated gp120 preparation was >95% pure, as demonstrated by polyacrylamide gel electrophoresis (Müller et al., 1988).

Antiretroviral Assay

The methodology used for the HIV-1 assay has already been described (Sarin et al., 1987). Cells of the human T-lymphoblast line CEM (seed concentration: $1 \times 10^5$ cells/ml) were suspended in medium and infected with the HIV-1 virus (strain $HTLV_{IIIB}$). For this purpose, 50 times a 50% cell culture infection dose [$CCID_{50}$] was chosen. A $CCID_{50}$ is the infectious dose at which 50% of the cells per ml of cell suspension are infected. 1 ml cultures were incubated for 5 days. Flupirtine was added to the cells in different concentrations 2 hours prior to infection. The number of living cells was determined by using the 3-[4,5-dimethylthiazol-2-yl]-2,5-diphenyltetrazolium bromide [MTT] colorimetric assay (Scudiero et al., 1988). An ELISA reader was used for the evaluation, as published earlier (Müiller et al., 1991). After incubation, the noninfected CEM cells underwent 2.16 and the infected cells 0.13 cell division cycles.

Blood Samples

Samples of human peripheral blood were taken (i) of 12 HIV-1 infected homosexual men [mean age: 35 years; range: 22–43 years], and (ii) of 8 healthy, HIV-1 seronegative men otherwise exposed to the same risks of almost the same age group (mean age: 30 years; range: 23–35 years). The patients were categorized according to the classification of the Centers for Disease Control (CDC, 1992). The studies with HIV-1 seropositive patients were carried out with blood samples of asymptomatic virus carriers (CDC: A1, A2, mean CD4 cell number 407 /μl, range: 209–698 /μl). None of the patients showed any sign of tumours, symptomatic infections, or had undergone immunosuppressive treatment, for example with corticosteroids, during the 10 weeks prior to the blood sample being taken.

Cell Preparations and Treatment thereof

Mononuclear cells [MNC] were obtained from heparinized blood by centrifugation using a Ficoll-Hypaque density gradient, and enriched (Rossol et al., 1990). $0.5 \times 10^6$ cells were cultivated in culture medium in an end volume of 500 μl; the medium used was MEM-medium enriched with 10 mM HEPES buffer, 2.6% sodium bicarbonate, 100 U/l penicillin, 100 μg/ml streptomycin, 10% foetal calf serum [FCS] and 1 mM glutamate. Where stated, cells were treated with the chemical substance immediately after isolation.

Induction of Apoptosis with Reactive Oxygen

Reactive oxygen radicals were produced by using the hypoxanthine [HX] and xanthine oxidase [XOD] system (Bruck et al., 1994).

MNCs were suspended for 24 hours in a total volume of 500 μl of MEM medium (as described above).

0 to 80 mU/ml XOD and 1 mM HX were added to this batch. At a concentration of 90 mU/ml XOD (Sigma, Munich, Germany), >90% of lymphocytes suffered apoptotic cell death.

Unless stated otherwise, 10 mU/ml of the enzyme XOD and 1 mM HX were used for the following studies. Under these incubation conditions, about 50% of the cells underwent apoptosis. It is favourable to maintain this level of apoptosis when examining whether a certain compound is a potential inhibitor and/or stimulator of apoptotic cell death. Flupirtine was added to the cells 6 hours prior to the addition of the oxygen radical producing system; the incubation was terminated after one day.

Analysis of Cells by Continuous Flow Cytometry

Apoptosis was measured in a FACScan (Becton-Dickinson) continuous flow cytometer with argon laser excitation at a wavelength of 488 nm, according to the published method (Schmid et al., 1994). The lymphocytes were separated and characterized by optical methods, using a combination of forward light scattering as a measure of the size of the cells [FSC] with orthogonal scattering as a measure of the surface constitution [SSC]. To stain apoptotic MNC-cells, these were incubated with 20 µg/ml of 7-aminoactinomycin D [7-AAD] (Sigma) dissolved in PBS, at 4° C. in darkness for 20 minutes. Subsequently, the cells were analyzed with the continuous flow cytometer in the dye solution. The red fluorescence caused by 7-AAD was detected using a filter of the wavelength of 650 nm.

Owing to disintegration of the cell membrane, 7-AAD penetrates apoptotic cells and subsequently stains the DNA by an intercalation process. The data were analyzed using the LYSIS II program.

The mean channel counts were converted into mean fluorescence intensity, cell size and surface constitution.

In Situ Fluorescence Labelling by the TdT Method and Surface Labelling

To define a certain cell subpopulation undergoing an apoptotic process, the cells were treated with the terminal transferase system [TdT]. The method of Gorczyca et al. (1993) was used with minor modifications. Cells in suspension were washed twice in PBS (Gibco) and subsequently fixed in 1% strength para-formaldehyde (Riedel de Haen) at 4° C. for 10 minutes. The cells were then washed twice in PBS [to which 5% AB serum and 0.5% bovine serum albumin (BSA) had been added]. The cells were then pelleted and resuspended in 50 µl of 2.5 mM cobalt chloride solution, to which 0.5 nM biotin-16-dUTP and 25 U TdT had been added. This batch was buffered with 200 mM potassium cacodylate, 25 mM Tris-HCl and 0.25 mg/ml BSA; the incubation took place according to the directions of the manufacturer (Boehringer Mannheim, Mannheim, FRG) at 37° C. for 30 min. The cells were subsequently washed twice in PBS [5% AB serum and 0.5% BSA] and resuspended in 100 µl of a buffered dye solution containing 5 µg/ml fluorescent isothiocyanate [FITC] labelled avidin [cell analytical reagent quality]. For simultaneous surface labelling the cells were additionally treated with 20 µg/ml phycoerythrine labelled monoclonal anti-CD3-antibodies (Becton-Dickinson).

The fluorescence was quantified by continuous flow cytometry as described by Halliwell (1987).

Results

Treatment of HIV-1 Infected CEM-cells with Flupirtine

CEM-cells were pretreated with flupirtine for 2 hours and subsequently remained noninfected or were infected in a parallel experiment with HIV-1.

After 5 days the numbers of cells in the relevant experiments were determined. FIG. 1 shows that the concentration of cells in noninfected or infected cultures did not vary significantly (P>0.1) as a result of treatment with flupirtine.

Flupirtine was added to the experiments in final concentrations of between 0.1 and 30 µg/ml. The cell concentration in the noninfected experiments was 446,880±31,020 cells/ml, in the HIV-1 infected experiments it was 108,420±6,710 cells/ml.

These results show that flupirtine has no toxic effect on the cells, but neither does it affect HIV-1 infection in vitro under the incubation conditions employed.

Adjustment of the Hypoxanthine/Xanthine Oxidase Systems

The xanthine oxidase concentration [XOD] was selected in such a way that the proportion of apoptotic cells came out at about 50%.

Apoptotic cells display a fluorescence intensity of >10 arbitrary channel counts. At 0 mU of XOD, only 6.6±2.1% of the cells were above this cut-off line of >10 arbitrary channel counts, i.e. 6.6% were apoptotic. With increasing concentrations of XOD the percentage of apoptotic cells increased and, at 80 mU XOD, reached a value of 93.2±6.8% of apoptotic cells. At 10 mU XOD, about 50% (to be precise, 54.6±6.1%) of the cells underwent an apoptotic process.

In the absence of XOD the cells displayed an FSC/SSC distribution pattern as follows:

Cell size 349±27 (arbitrary channel count) with a surface constitution of 112±15. At an enzyme concentration of 80 mU, the size of the cells decreased and reached a value of 256±22, while the degree of surface constitution increased to 180±29. Such changes indicate a characteristic apoptosis, based on morphological changes of the cells. At 10 mU XOD, the cells displayed a distribution pattern midway between the aforementioned extremes. Unless stated otherwise, 10 mU of enzyme were used.

Effect of Flupirtine on the Spontaneous Rate of Apoptosis in Human Lymphocytes

Peripheral blood MNCs of healthy subjects and HIV-1 infected patients were examined for spontaneous apoptosis. The cells were analyzed one day after the blood samples of the subjects had been taken. As is evident from FIG. 2, 6.32±0.82% of MNC cells of the control groups of noninfected subjects exhibited apoptosis after this time, while 28.42±7.84% of the cells of HIV-1 infected patients underwent apoptosis. MNCs of both groups were treated for 24 hours with flupirtine at concentrations of 0.1 to 30 µg/ml. As summarized in FIG. 2, the rate of spontaneous apoptosis of lymphocytes did not change significantly (P>0.1) under the effect of flupirtine. This is true for cells of healthy subjects and HIV-1 infected patients.

Reduction of Induced Apoptosis in Mononuclear Cells due to Flupirtine

MNCs of healthy subjects and of HIV-1 infected patients was treated with the HX/XOD system (formation of oxygen radicals) to induce apoptosis. Flupirtine in different concentrations was added to the cell cultures 6 hours prior to exposition to the inductor. As is evident from FIG. 3, flupirtine concentrations between 0.1 and 3.0 µg/ml brought a significant reduction of apoptotic cell death (P<0.001). At a flupirtine concentration of 10 µg/ml, the protective effect was only significant in assays of lymphocytes of infected subjects. At concentrations of from 0.3 to 3.0 µg/ml flupirtine, the protective effect of the drug was most pronounced, and inhibition of induced apoptosis was strongest. The reduction of induced apoptosis in the experiments with lymphocytes of healthy subjects was about 40% and in those of HIV-1 infected patients about 60%.

Apoptosis in lymphocytes was also detected using the DNA-fragmentation method. After incubation of the cells with the HX/XOD system, the DNA was extracted from the cells, separated according to size in agarose gel and subsequently transferred to a blot.

The DNA disintegrated into a ladder-like pattern of fragments of 180 base pairs and multiples thereof. Such a fragmentation pattern is characteristic of DNA destruction in apoptotic processes (Wyllie, 1980). In contrast, cells which had been treated with 1 µg/ml flupirtine did not show any DNA fragmentation.

Representative dot blots showing the effect of flupirtine on cells undergoing spontaneous and induced apoptosis were likewise obtained.

To carry out this series of experiments, apoptosis was induced in MNCs using the HX/20 mU XOD system. Under these conditions—in the absence of flupirtine—64.2±7.9% of the cells became apoptotic.

However, when these cells were treated with flupirtine for 24 hours, the proportion of apoptotic cells decreased significantly to 18.3±5.8%.

These results clearly show that flupirtine is a promising medicaments for example for the treatment of induced apoptotic cell death of lymphocytes in AIDS patients.

DE-A-43 27 516 describes the neuroprotective action of flupirtine, for example in cerebral ischaemia, Alzheimer's disease, Parkinson's disease and neurodegenerative disorders induced by infection such as AIDS encephalopathy or Creutzfeld-Jakob disease.

AIDS encephalopathy with progressive dementia is a neurological complication of AIDS. One of the causes of AIDS encephalopathy is thought to be the HIV(gp 120)-induced release from infected macrophages of NMDA agonistic neurotoxins such as quinolinic acid, finally leading to mortification of the nerve cells.

AIDS encephalopathy and AIDS itself (acquired immunodeficiency syndrome) are diseases affecting different organ systems. The former is, as already described, a neurological complication of AIDS (apoptosis of nerve cells), while the latter is based on a disorder of the cellular immune system with a pronounced reduction in the number of T cells (apoptosis of a constituent of the haematopoetic cell system).

The effect of flupirtine according to the invention, i.e. the inhibition of induced apoptosis of cells of the haematopoetic cell system, for example lymphocytes, was all the more surprising as the existence of NMDA receptors outside the central nervous system had hitherto not been demonstrated. Therefore, even a person skilled in the art could not have foretold the protective effect of flupirtine on the cells of the haematopoetic cell system on the basis of its protective effect on nerve cells.

Other diseases which can be treated prophylactically or therapeutically on the basis of the effect of flupirtine according to the invention are for example:

neutropenia/lymphocytopenia induced by drugs (such as cytostatics and corticosteroids), toxins, radiation or other diseases thrombocytopenia induced by drugs or infections (for example HIV).

Flupirtine can be administered for prophylaxis and therapy in known manner in the following forms:

tablets, film-coated tablets, hard gelatine capsules, soft gelatine capsules, pellets, granules, sugar-coated tablets, suppositories, microcapsules, water- or oil-based suspensions, oil-based solutions, injectable solutions for intramuscular administration, injectable solutions for intravenous administration.

Suitable salts for the preparation of the medicament are all physiologically compatible salts of flupirtine. These are for example the hydrochloride, maleate, sulphate and gluconate of flupirtine.

The contents of flupirtine in the medicaments according to the invention is 0.1 mg–3000 mg, preferably 10 mg–500 mg. The stated single dose of the medicament can be administered 1–5 times daily, preferably 1–3 times daily.

The dosages stated always relate to flupirtine as base. When salts of flupirtine are used, a conversion taking into account the molecular weight is necessary.

The compounds according to the invention are pharmaceutically processed according to customary standard methods. For example, flupirtine and the excipients and/or auxiliaries are thoroughly mixed by stirring or homogenization, in general at temperatures between 20 and 80° C., preferably 20 to 50° C.

Figure 1:
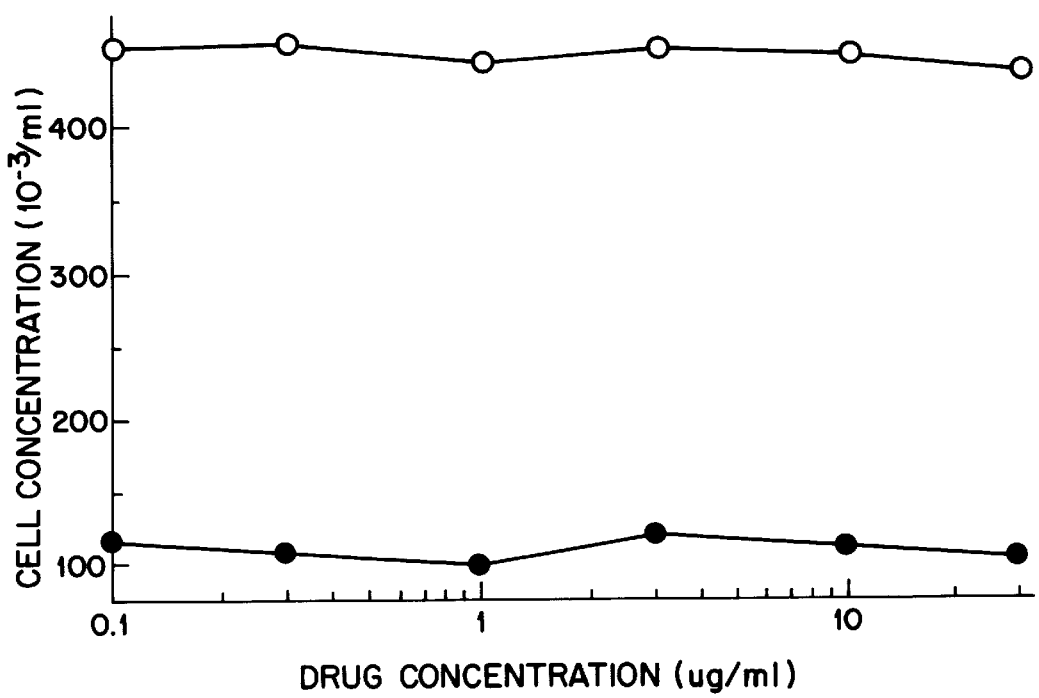
FIG. 1
Figure 2:
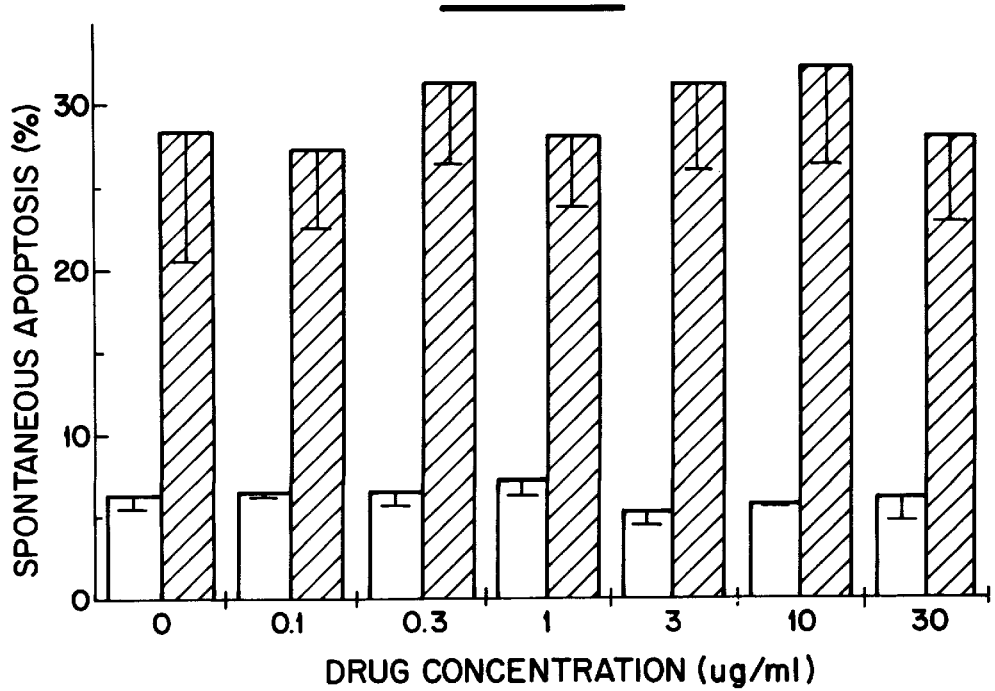
Figure 3:
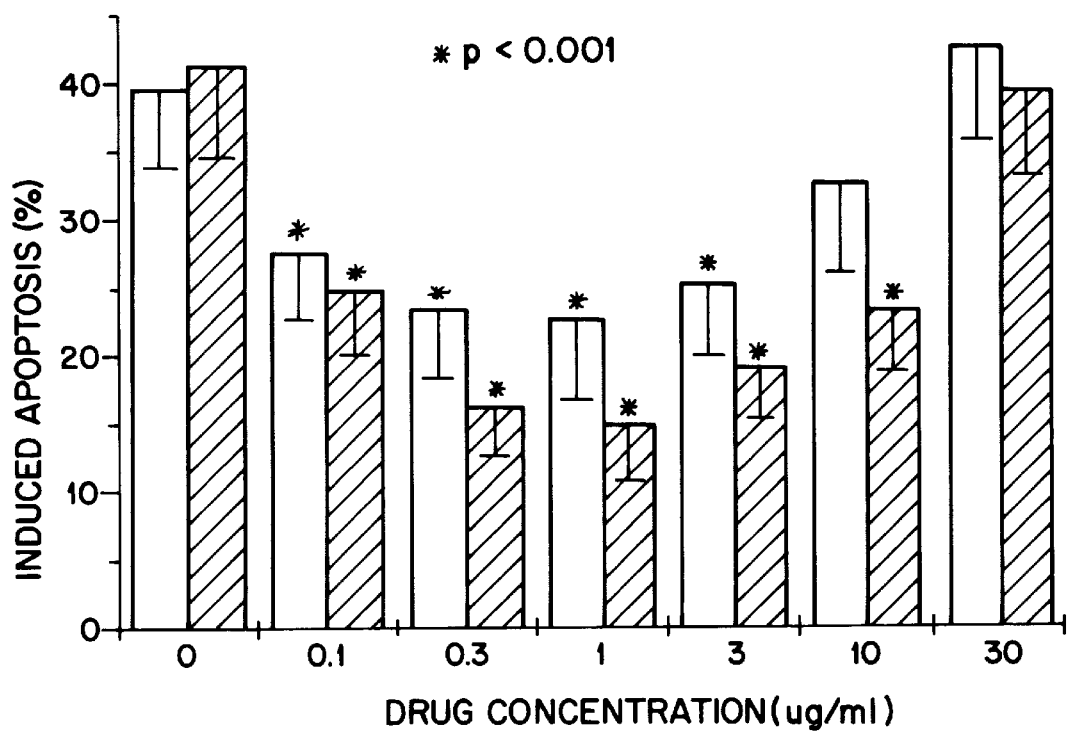

Incubation of noninfected [○] and HIV-1 infected CM-cells [●] with different concentration of flupirtine. Stated are the mean values of 10 experiments run in parallel; the standard deviations were not higher than 10%.

FIG. 2

Effect of flupirtine on the spontaneous apoptosis of lymphocytes of noninfected subjects [open bar] and HIV-1 infected patients [diagonally hatched bars]. After one day, the cells were analyzed by constant flow cytometry. Examined were lymphocytes of 12 infected patients and 8 noninfected subjects; the mean values and the standard deviations are stated.

FIG. 3

Reduction of induced apoptotic mortification of lymphocytes after treatment with flupirtine. Apoptotic mortification of MNCs of noninfected subjects [open bars] and HIV-1 infected patients [diagonally hatched bars] was effected by employing the HX/XOD-system. Flupirtine was added to the cells 6 hours prior to the oxygen radical generating system. One day later the cells were analyzed by continuous flow cytometry. The values for total apoptosis were determined; subtracted therefrom were the values for spontaneous apoptosis. The values depicted therefore indicate the extent of induced apoptosis. Lymphocytes of 12 infected patients and 8 noninfected subjects were examined; mean values and standard deviations are stated.

References cited herein are hereby incorporated by reference.

What is claimed is:

1. A method of treating hematopoietic associated apoptotic cell death, in a patient in need of such treatment, said method comprising administering a hematopoietic associated apoptotic cell death treating amount of flupertine or a pharmaceutically useable salt thereof to an individual.

2. The method of claim 1 wherein said flupertine or pharmaceutically usable salt thereof is combined with pharmaceutically suitable excipients or auxiliaries to form an appropriate administration form.

3. The method of claim 1 wherein flupertine is administered in an amount between 10 mg and 2.5 g per day.

* * * * *